United States Patent [19]
Johnston et al.

[11] Patent Number: 6,106,732
[45] Date of Patent: Aug. 22, 2000

[54] INTEGRAL BLOOD PLASMA OR SERUM ISOLATION, METERING AND TRANSPORT DEVICE

[75] Inventors: James Bennett Johnston, Ambler; Kenneth Grady, Phoenixville, both of Pa.

[73] Assignee: Binax Services, Inc., Portland, Me.

[21] Appl. No.: 09/060,885

[22] Filed: Apr. 16, 1998

[51] Int. Cl.[7] ............................. B01D 37/00; G01N 33/49
[52] U.S. Cl. ......................... 210/767; 210/503; 210/504; 210/505; 210/508; 422/56; 422/57; 422/58; 436/169; 436/170; 436/177
[58] Field of Search ..................... 210/503, 505, 210/508, 509, 767; 422/55, 56, 57, 58; 436/170, 177, 178, 169; 435/2

[56] References Cited

U.S. PATENT DOCUMENTS

| | | | |
|---|---|---|---|
| 4,477,575 | 10/1984 | Vogel et al. | 436/170 |
| 4,816,224 | 3/1989 | Vogel et al. | 422/55 |
| 4,933,092 | 6/1990 | Aunet et al. | 210/729 |
| 5,135,719 | 8/1992 | Hillman et al. | 422/101 |
| 5,262,067 | 11/1993 | Wilk et al. | 210/767 |
| 5,558,834 | 9/1996 | Chu et al. | 422/55 |
| 5,589,399 | 12/1996 | Allen et al. | 436/169 |
| 5,641,682 | 6/1997 | Pagels et al. | 436/43 |
| 5,798,272 | 8/1998 | Allen et al. | 436/169 |

FOREIGN PATENT DOCUMENTS

0 295 526  12/1988  European Pat. Off. .

*Primary Examiner*—John Kim
*Attorney, Agent, or Firm*—The M.H. Sears Law Firm Chartered

[57] ABSTRACT

A process for separating plasma or serum from mammalian whole blood includes the steps of applying a sample of blood through a hydrophobically faced sample receiving hole positioned in a first upper layer of hydrophobic material to a first layer of fibrous hydrophilic material which has been impregnated with a blood agglutinating agent so that it acts to retain red blood cells but not plasma or serum and layer is sealed at its upper edges to the first layer of hydrophobic material and allowing the liquid portion of the sample to flow downwardly through the first layer of fibrous hydrophilic material into a second layer comprised of a different fibrous hydrophilic material which second layer is sealed at its lower edges to a second layer of hydrophobic material whereby it acts to retain the plasma or serum.

8 Claims, 4 Drawing Sheets

Definition of Angle Theta (θ)

INTEGRAL BLOOD PLASMA OR SERUM ISOLATION, METERING AND TRANSPORT DEVICE

FIELD OF THE INVENTION

The present invention relates to an improved device for the collection of mammalian, including human, blood and the separation therefrom of defined volumes of plasma or serum, which device is capable of maintaining said plasma or serum in stable condition without refrigeration during transportation, e.g., by mail, to a remote location for quantitative or qualitative assay in a laboratory. More particularly, with the present invention, collection of the blood samples can be performed without the services of a professional phlebotomist (or other medical professional) and separation of the plasma or serum therefrom is effected without the need for centrifuges or other mechanical devices. In addition, the device of the present invention receives an unmetered volume of whole blood, separates the plasma or serum from the red cells and then meters a defined volume of the plasma or serum into the sample pad. This plasma or serum sample is stabilized on the pad and is protected from contamination until it can be suitably assayed in a laboratory that may be remote from the collection site.

BACKGROUND OF THE INVENTION

There are many contexts in which the ability to assay mammalian blood plasma or serum is extremely important. Firstly, the diagnosis and/or monitoring of many pathological conditions requires such an ability, as does the monitoring of certain pharmaceutical regimens. Secondly, in human beings, such an ability may be important to permit a well-founded assessment of a person's fitness to undertake certain forms of intensive physical activity, such as certain forms of athletic activity. In some of these instances, assay of a single sample of plasma or serum for a given constituent, e.g., a ligand, may provide the desired information; in others, it is important that a series of plasma or serum samples collected at stated intervals or after defined events, such as levels of heart-rate raising exercise or intake of food or medicine, may need to be assayed to provide the desired information.

At present, there are well established means for the collection of whole blood samples and for transport of these samples to a laboratory, followed by processing to separate the red cells from the plasma and analysis of the blood plasma portion thereof to make a qualitative or quantitative assessment as to one or more actual or suspected components thereof. For example, the collection of venous blood in sterile vacuum tubes such as Vacutainer® brand tubes is well known. But such blood collection requires the services of a trained health professional, such as a nurse, doctor or professional phlebotomist. It is often extremely inconvenient for a mammalian patient to attend at a blood collection site, as well as costly. When it is necessary to collect a series of blood samples from the same subject over intervals of time, moreover, inconvenience and cost are greatly multiplied.

In addition, samples of liquid blood, plasma or serum usually require refrigeration and expeditious transport to the analytical laboratory if their integrity is to be maintained. Despite a variety of chemical stabilizers available in collection tubes such as Vacutainer® tubes, sample stabilities often are only about 48 hours and commonly this storage time is achieved only when the tubes are kept under refrigeration.

Numerous simple devices are also in use for separation of red blood cells from plasma or serum immediately after the collection of a whole blood sample from a mammalian subject. These devices generally operate on a lateral flow chromatographic principle and are so designed that the separated plasma or serum is immediately subjected to a qualitative or quantitative assay for at least one ligand, often by use of a "throwaway", one-use-only, device pre-impregnated with a binding partner for each ligand to be assayed. Such devices typically provide for lateral flow of the sample along a pre-impregnated pathway and for development of a color reaction when the ligand assayed for is present. In some of these cases the blood separation device and subsequent plasma or serum assay device are constructed as a single disposable unit—but in all such cases the object is to obtain a plasma or serum sample and assay that sample while the mammalian patient is present in the medical practitioner's office. Descriptions of blood separation devices of the lateral flow, chromatographic genre appear, inter alia, in U.S. Pat. Nos. 5,135,719; 4,816,224; 4,477,575; 5,186,843; 5,262,067; 4,933,092 and European patent 0295526. In these and similar known blood separation devices, media used in the separation step include various fiberglasses, composite products of the types, e.g., sold under the registered U.S. trademarks Hemasep and Cytosep, and other hydrophilic fibrous materials having effective pore sizes slightly larger than the hydrodynamic volume of a red cell. In general, the physical dimensions and arrangement of the fibers in these media are such that they impede the flow of red blood cells at the surface to which the blood sample is applied while allowing relatively unimpeded flow of the plasma or serum by capillarity. While the red cells are able to move through the fibrous matrix, their flow rate is much slower than that of the plasma or serum, resulting in the formation of a red-cell-free zone at the leading edge of the flow. Because the plasma or serum volumes supplied by separations effected with these devices are somewhat variable, quantitative assays for ligands using such plasma volumes require the development and use of a calibration curve for each specific ligand being determined. Because such calibration curve development is time-consuming and tedious, and somewhat impractical of performance in many point-of-care milieus, such as medical practitioners' offices, the serum or plasma volume separated by these devices is, as a practical matter, most often subjected to a qualitative assay for the presence of the target ligand.

Simple devices are also known that permit blood sample collection, stabilization and transport, such as depositing a drop of peripheral blood onto a sheet of filter paper and allowing it to dry. Such a device is currently used for qualitative detection of inherited diseases in newborns, such as phenylketonuria. More recently, a similar "test card" comprising filter paper has been suggested for a commercial, mail-in system for the qualitative detection of HIV antibodies in whole blood. Thus, U.S. Pat. No. 5,641,682 refers to a test card of this type supplied in a commercial over-the-counter kit. The person desiring an HIV test is directed to place multiple whole blood spots on the card, allow them to dry, and then to convey the card containing dried blood spots to a laboratory where an assay for HIV antibody is performed. This simpler means of whole blood collection does not require the services of a trained phlebotomist. It suffers from two main disadvantages, however: first, it does not allow for the collection of a defined volume of blood, blood plasma or serum; and second, mere drying of whole blood may not adequately stabilize the blood constituents from the time of collection to the time of assay. Quantitative assays for various substances in plasma or serum, such as antibodies, enzymes, hormones, drugs and small molecular weight constituents such as glucose, cholesterol, or lactic acid, require a knowledge of the plasma or serum sample volume. Dried whole blood samples contain an unknown volume of blood plasma or serum. The plasma or serum volume contained per unit area of a dried blood spot varies according to the hematocrit of the sample and as a result of the duration and other conditions of the drying process; the plasma or serum volumes resulting from lateral chromatographic separation of red cells and plasma have been found to be highly variable. Other sources of variation can be related to the uniformity or lack thereof, and other characteristics of the collection matrix, among other factors.

SUMMARY OF THE INVENTION

The present invention embodies a collection device that can reliably be used by anyone without special training of any nature for the collection of one or more samples of mammalian whole blood. This device in its simplest form comprises a single blood-receiving port that has been formed in an upper layer which comprises hydrophobic material, which layer is firmly bonded to an underlying suitable hydrophilic layer impregnated with a blood agglutinating or clotting agent. This hydrophilic layer is in contact with an underlying second hydrophilic layer into which it reliably meters a defined volume of plasma or serum, whereupon the two upper layers are mechanically stripped away and the plasma or serum in the second hydrophilic layer is allowed to dry. The second hydrophilic layer is underlaid with a second hydrophobic layer which, inter alia, aids in the retention of the plasma sample within the second hydrophilic layer during the drying period. In the separation step conducted in the first hydrophilic layer and during transfer of a metered volume of the serum or plasma into the second hydrophilic (plasma retention) layer, the capillary flow of serum or plasma is vertical rather than lateral and hence the flow path is short in relation to the known lateral flow separation devices.

This use of a vertical flow principle to separate the serum or plasma from the red cells and meter a defined volume into the second hydrophilic, or plasma retention, layer is an important aspect of the device of this invention.

For mailing or other transport to a laboratory, the device of this invention, the plasma or serum retention layer is covered with a protective cover so arranged as to permit air to circulate over and contact the sample retention layer even when the cover is closed.

Simple tests and, in some instances, other criteria for the individual layer components are more particularly described hereinafter.

The device may be constructed with multiple whole blood sample-receiving stations, each comprising two layers of hydrophilic material sandwiched between two layers of hydrophobic material as described.

After the blood collection, separation and metering for all sample-receiving stations is complete, so that the two upper layers have been stripped away and the plasma (or serum) retention layer has been air dried at each station, preferably while covered as hereinafter more fully described, the device is closed with the individual station covers in place and the entire device is preferably sealed into a resealable, zip-lock or similar pouch containing a desiccant. This pouch and desiccant aid in maintaining sample stability during mailing or other transport to a laboratory in that they maintain dryness of the plasma retention pads as well as providing barriers to contamination, sunlight, artificial light, humidity and other adverse, frequently variable, environmental factors.

When the device of the invention is received at a laboratory the hydrophilic sample retention pad (second hydrophilic layer) is stripped away from the underlying second hydrophobic layer. The dried plasma or serum may then be extracted into any of various suitable media and analyzed for known or suspected target constituents. Alternatively, the sample retention pad can be placed in contact with the reaction pathway of a device adapted to conduct a preselected immunospecific assay, wetted with a suitable buffer or other appropriate liquid and subjected to the assay.

Specific analytical modalities and immunoassays are well known and are not within the scope of this invention. The plasma retention pad of the present invention, in general, can be treated by known extraction and/or contact methods so as to enable analysis or assay of the plasma sample by any of the well known modalities for effecting it.

DETAILED DESCRIPTION OF THE INVENTION

Early in the work which led to the present invention, it was discovered that the separation media employed in the various devices which separate the red cells from plasma or serum using a lateral flow chromatographic principle as mentioned hereinabove are unsuitable for obtaining a defined volume of red-cell-free serum or plasma from a whole blood sample. "Defined volume" as used herein, means the volume of plasma, as determined from a standard curve for L-lactate in fresh, red-cell-free plasma obtained as shown in Example 2 hereof, that when analyzed by the same method gives, within the limits of experimental error (taken as a coefficient of variation not exceeding 6.0) the same L-lactate content in millimoles as was obtained by analyzing 6 µL. of fresh red-cell-free plasma. Thus, while defined volume as so used is not reproducible to a mathematical preciseness of two decimal places, it is a volume that is sufficiently consistent and reproducible that comparable analytical and/or assay results, well within the experimental error of the available analytical and assay methods, are regularly obtained.

The early work on blood separation media employed in the blood separation devices that utilize the lateral flow chromatographic principle showed three problems: to wit, (1) separation of a plasma zone that yields enough red-cell-free plasma for routine wet chemistry analysis of, e.g., glucose or L-lactate content was slow, taking 10–30 minutes or more to yield an acceptable-sized red-cell-free zone; (2) the size of the red-cell-free zone varied considerably from sample to sample, whereby configuring a single geometry that would yield a minimum plasma volume, in the order of 2–10 µL. of plasma that was both isolatable and separable from the red-cell-containing zone was difficult to impossible; and (3) zones visually free of red cells that did form in these media did not contain an essentially constant volume of plasma per unit area.

When agglutinating agents as described in U.S. Pat. Nos. 4,933,052 and 5,135,719 and European patent 0295526 were added to these separation media, the only problem to some extent alleviated was the first one above—i.e., the speed of separation of red cells from plasma increased.

By measuring blood hematocrit in various samples, it was found that the second problem mentioned above is roughly related to hematocrit level (hematocrit being defined as the volume fraction of the packed red cell component of blood) in that the higher the hematocrit, the longer it takes for an essentially standard-sized red-cell-free zone to form in these lateral flow separation media.

Adding a plasma acceptor zone comprising a porous hydrophilic medium such as filter paper to various lateral flow separation media was also tried with the disappointing result that a highly variable volume of plasma per unit area was formed on the plasma acceptor medium. This was true even when an agglutinant was employed in the separation medium.

When, however, a vertical format device was made using a separation medium adopted from a lateral flow device and having an agglutinant therein and the separation zone was followed by a plasma capture medium, it was observed that a defined volume of plasma was sometimes captured in the capture zone.

Further efforts to arrive at a blood separation device capable of capturing a defined volume of plasma regularly and reproducibly led to the development of the four-layer "sandwich" consisting of a first hydrophobic layer, a first hydrophilic blood separation layer containing agglutinant or clotting agent, a second hydrophilic plasma capture layer and a second hydrophobic layer, which "sandwich" is the essence of the present invention. These efforts also led to the development along the way of criteria for the materials used in the various layers.

Blood separation media useful in this invention must be agglutinin or coagulating agent impregnated. Preferably the agglutinin is a mixture of a lectin with no blood group specificity, of which phytohemagglutinin P is most preferred and a polycationic chemical such as hexadimethrine bromide or poly-(1,1-dimethyl-3,5-dimethylene piperidinium chloride), with hexadimethrine bromide being preferred. Other lectins which may be substituted are lectins from wheat germ (*Triticum vulgaris*), potato (*solanum tuberosum*), soybean (*glycine max*) and that from the bacterium *Mycoplasma gallisepticum*. A suitable substitute for lectinpolycationic agent mixture is a mixture of a natural coagulating agent, such as thrombin or snake venom, with a polycationic agent or a cocktail of the type disclosed in U.S. Pat. No. 5,089,415. Other acceptable agglutinating and clotting agents will readily occur to those skilled in blood separation techniques.

The media that are suitable for the blood separation layer can be identified by a simple test as follows: A 2.5×0.5 cm. test strip of the candidate material is cut and placed on a cellophane tape-covered solid support, where it is held in place by a 1 cm. wide, 2 cm. long cellophane tape strip placed across the test strip at right angles in a location 0.5 cm. from the end of the test strip. A drop of whole blood of 50 µL. or greater volume, to which has been added a known anticoagulant, is placed on the cellophane in contact with the end of the test strip nearest the anchoring cellophane tape. This blood is allowed to chromatograph laterally through the test strip and is prevented from migrating over or under the test strip by the anchoring cellophane tape. If this chromatography produces a visual red-cell-free zone at its leading edge that is at least 2 mm. long, the medium of the test strip is suitable for use as the first hydrophilic blood separation layer of the device of this invention, once it has been impregnated with agglutinating or clotting agent.

Suitable media for the plasma capture and retention, or second hydrophilic layer are cellulosic filter papers, ion exchange papers, fiberglasses, nylons, certain grades of composite media such as Cytosep® and the like.

Figure 2:
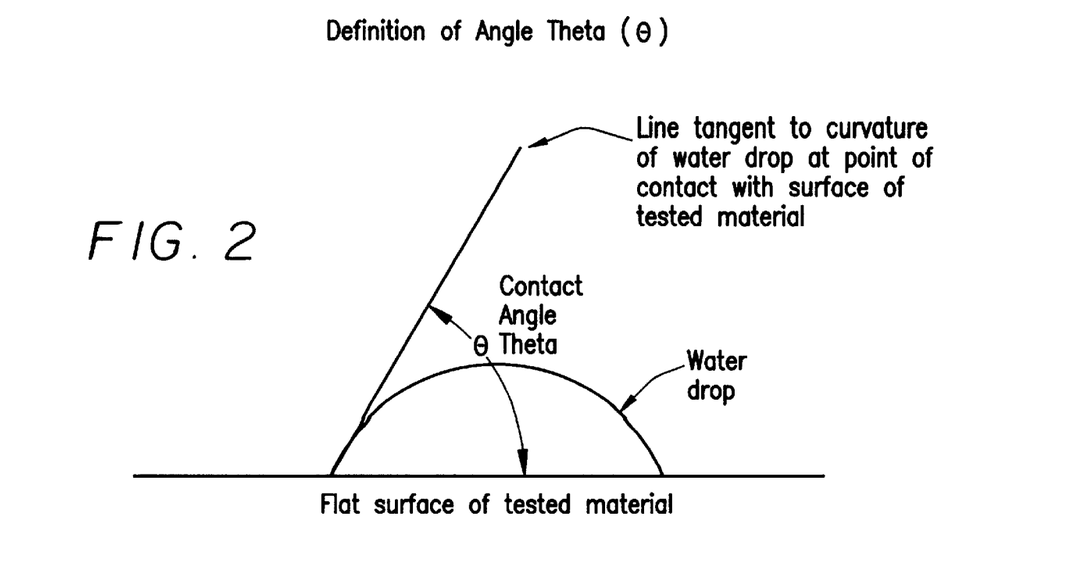
FIG. 2 illustrates the contact angle test with a water drop used to test hydrophobicity of proposed materials to determine their acceptability to be used in the devices of this invention as hereinafter described.

The hydrophobic layers which abut the top of the blood separation layer and the bottom of the plasma capture and retention layer may be of the same or different material. Suitable materials are those which meet the following test:

A drop of water is carefully placed on a horizontal, flat surface of the candidate material. This drop of water will form a bead on all suitable materials and will rapidly assume a shape as depicted in FIG. 2 hereof in which the edge of the drop forms an angle $\ominus$ with the flat surface of the candidate material at the point of their contact. Materials sufficiently hydrophobic to be used in the hydrophobic layers of the device of this invention exhibit a minimum contact angle of 60 degrees, preferably 80 degrees and most preferably 85 degrees. See, e.g., Myers, D, in *Surfactant Science and Technology*, pp. 305–306 (VCH Publishers, New York, 1988).

If a candidate material has an adhesive or other coating, the test must be performed on the coated surface. It has been found that a coated material that passes the test on its uncoated surface but is hydrophilic on the coated surface will, if used as the second hydrophobic layer, prevent capture/retention of a defined volume of plasma in the plasma capture and retention layer.

Among suitable hydrophobic materials are cellophane tape, polyethylene, any solid plastic material that meets the hydrophobicity test and is heavy enough to act as a solid base support and any hydrophobic plastic tape that is affixed to a solid base such as cardboard.

In fabricating the device, certain precautions must be taken. The first hydrophobic layer and the whole blood separation layer must be firmly bonded together at the edges so as (1) to prevent red blood cells from migrating around the edges of the blood separation layer and contaminating the plasma collection and retention layer, and (2) to provide a means for ready mechanical separation of the blood cell separation layer from the plasma collection and retention layer.

One means of effecting this bonding is to heat seal the edges of the first hydrophilic, blood separation layer to a polyethylene coated solid support. The two hydrophobic layers attached to base supports each extend well beyond the edges of the two hydrophilic layers at every blood receiving station. Means must be provided at each station to hold those portions of these hydrophobic layers that extend beyond the bounds of the hydrophilic layers firmly in contact with one another so that they will (1) keep the two hydrophilic layers in firm, uniform, surface-to-surface contact during blood sample application, separation and the wicking of the plasma into the lower hydrophilic layer and also (2) allow subsequent, facile mechanical separation of the two solidly supported hydrophobic layers so that there is isolation of the plasma in the plasma retention layer. A wide variety of such means are known for this purpose and any of them that will perform the necessary functions is acceptable.

Means that have been tested successfully include creating the base supports out of strips of cardboard, and spot gluing the supports together, cardboard to cardboard, on opposite sides of the blood sample application hole, about 1 cm from its edge. To separate the supports after the plasma sample has been captured, the strips are simply pulled apart, tearing the paper surface of the cardboard at the glue spots. Another preferred means is to utilize a double sided tape for the second or lower hydrophobic layer, mounting it on a cardboard base. If this hydrophobic layer is extended about 1 cm beyond the edges of the adjacent hydrophilic layer, it can be pressed to the inner surface of the first or top hydrophobic layer, holding the two support bases together. After the plasma has saturated the second hydrophilic (retention) layer, the plasma sample may be isolated by pulling the supports apart.

Figure 1A:
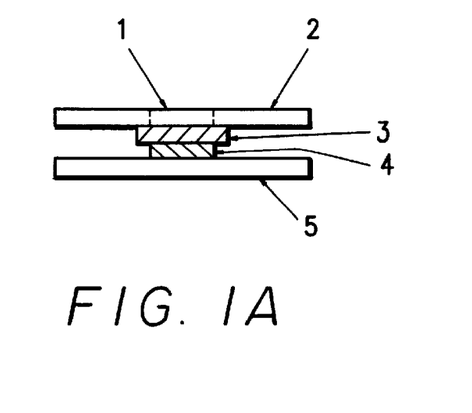
FIG. 1A is a side view of one blood receiving station according to the present invention as it exists prior to the application of a whole blood sample.

In general, the device requires the creation of a sandwich of two hydrophilic, porous media designated (3) and (4) in FIG. 1A, surrounded by layers marked (2) and (5) that are hydrophobic, relative to the porous media, and where one side of the upper hydrophilic layer, the sample-application side, is initially in contact with air, through hole (1). Thus, the blood sample applied at (1) begins to move through (3) by capillary action, but red cells are agglutinated there and become trapped. Plasma, in contrast, continues to flow through and makes contact with hydrophilic layer (4) and is drawn into it by capillary action. The plasma sample eventually saturates the voids of (4), thereby metering a defined plasma sample volume. The hydrophobic environment of the layers (2) and (5) that surround the edges of (3) and (4) does not itself absorb plasma. Moreover, the hydrophobicity of these layers appears to prevent the creation of a capillary force in the space between them. Without a capillary force, plasma is retained only in the hydrophilic plasma capture layer and a defined volume of plasma is obtained.

Figure 1B:
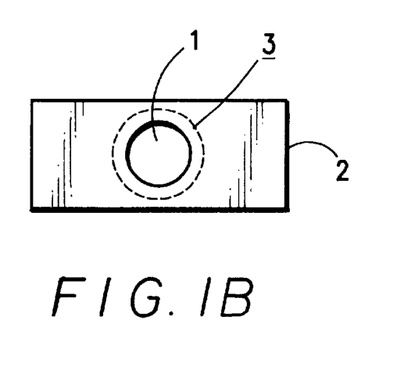
FIGS. 1B and 1C are top views, respectively, of (1) the upper hydrophobic layer and attached first hydrophilic or blood sample receiving layer and (2) the lower hydrophilic layer with appended lower hydrophobic or plasma retention layer after mechanical separation of these units from each other.
Figure 1C:
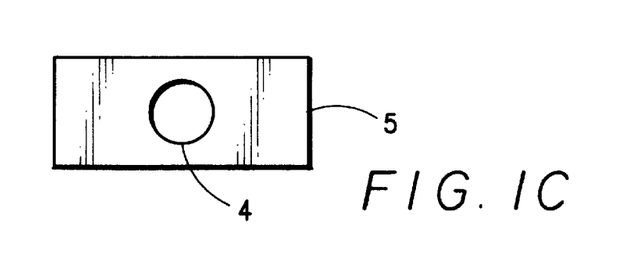

Separation of the hydrophobic layers which are either attached to neutral supports like cardboard (not shown in FIG. 1) or are thick enough to act as supports, isolates the plasma sample in (4). The surface-to-surface vertical flow separation format, moreover, allows no free liquid plasma to contact (4). Thus, when the hydrophobic layers are separated, there is no variable partition of liquid plasma into (4) as there would be, for example, if a strip of (4) were dipped into a drop of excess liquid plasma and then removed. Experience has shown that dipping of hydrophilic material suitable for (4) into a drop of liquid plasma, and withdrawing it, does not capture a defined reproducible volume of the plasma. The essentially uniform, reproducible partition of plasma between (3) and (4) followed by timely separation of these layers from one another, is a particularly valuable feature of this invention.

To foster the intention of making the device of this invention reliably useable by almost any person, several other optional features may be added to the device. For example, an athlete wishing to determine his or her exercise-induced lactate levels will want to collect several blood plasma samples, one immediately following each bout of a set of increasingly rigorous exercise bouts. Thus, multiple blood receiving stations including means for isolating multiple blood plasma samples may be included in a single device and kit, instead of only one such station.

FIGS. 3A to 3G illustrate various aspects of a device of this invention having five sample receiving stations. This device may be used, e.g., by athletes training for endurance in competitive athletics. The quantitative relationship between exercise intensity and the level of lactic acid in the blood has been used for decades to optimize the training of elite, Olympic-level athletes, see Weltman, Arthur, *The Blood Lactate Response to Exercise* (Human Kinetics Press, Champaign, Ill. 1994). Such assessment requires that the blood sample be collected within less than two minutes of completing the exercise, i.e., sample collection on-site at the track, court-side, or the like, and that the red cells, which produce lactic acid in a non-exercise related way, be separated from the plasma within a few minutes. Other possible uses for a device as illustrated in FIGS. 3A to 3G are in periodic monitoring of the level of a therapeutic drug where blood samples on an hourly or other periodic basis must be tested, periodic monitoring of blood constituents such as cholesterol or for mass screening for constituents such as blood glucose or blood urea nitrogen (BUN). Other uses for a device of this invention with multiple blood-receiving stations will readily occur to those skilled in the art.

As illustrated in the FIGS. 3A to 3G inclusive, each sample receiving station is provided with a cover. This is to prevent contamination of unused or completed sampling means by spillage of blood or other contaminants. These figures also illustrate the use of a protective flap that covers the completed set of samples, and their individual covers, as a further aid that prevents inadvertent mechanical damage during shipment to the laboratory.

One other key feature of the design shown in FIGS. 3A to 3G is that the individual sample covers are arranged to allow air to circulate over the sample even when the cover is closed. This is intended to foster drying of the sample. After the sample receiving stations have all had samples applied to them in the manner herein described, the device is sealed in a re-sealable, zip-lock foil pouch that also contains a desiccant which is provided in the kit with the device. The pouch and desiccant foster the maintenance of sample stability by maintaining dryness during transport, as well as providing a barrier to adverse environmental factors like sunlight.

The additional optional features illustrated here promote the intended use of the devices of this invention by providing barriers to contaminations and adverse environmental factors such as humidity and light. There are a plethora of ways of providing such features which are well-known or obvious to those skilled in the art. Any or all of them can be added to an embodiment of the instant invention.

Figure 3A:
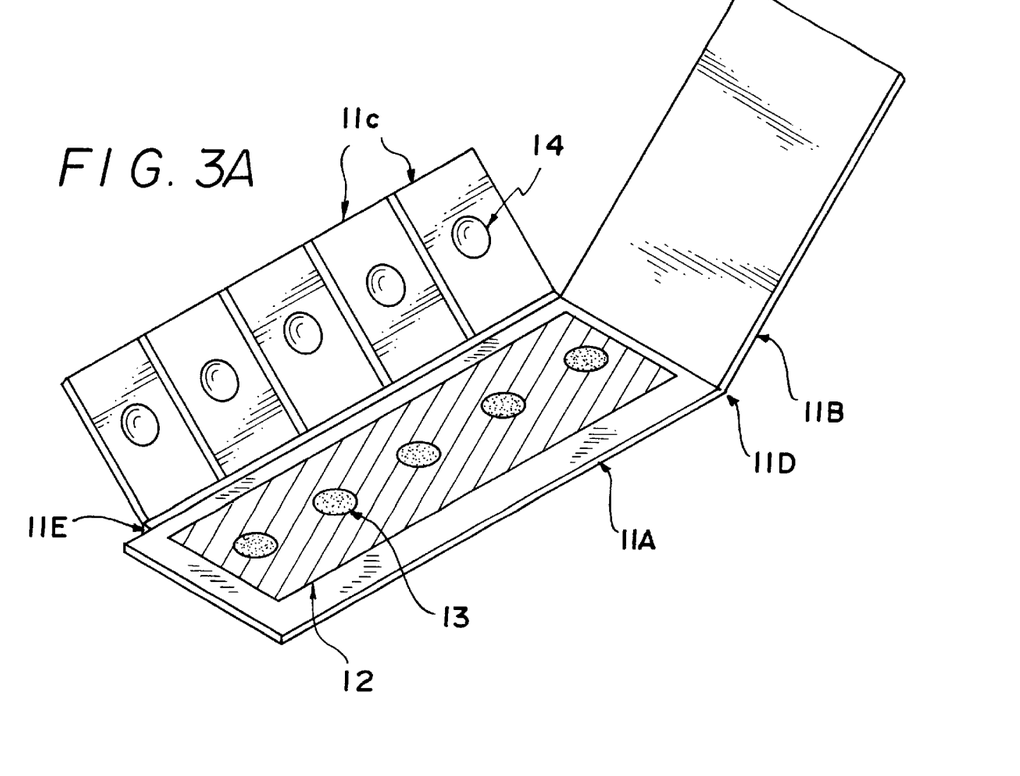
FIG. 3A depicts a typical device of this invention which is equipped with five blood sample receiving stations, as it appears during fabrication of the device with only the bottom hydrophobic layer and the second (plasma retention) hydrophilic layer, the latter in the form of five discs of material in place. The device also has this appearance when ready to send to a laboratory after separation of the upper hydrophobic and underlying first hydrophilic layers.
Figure 3B:
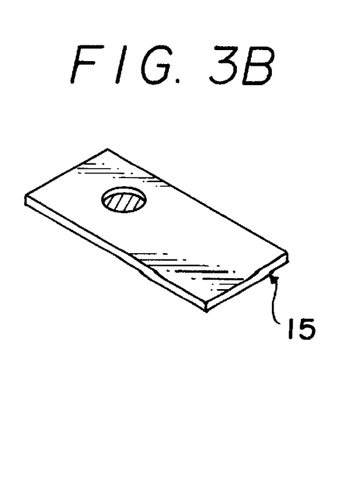
FIG. 3B depicts a single section of the preferred arrangement of the unit, fabrication detail of which appears in FIG. 3C.
Figure 3C:
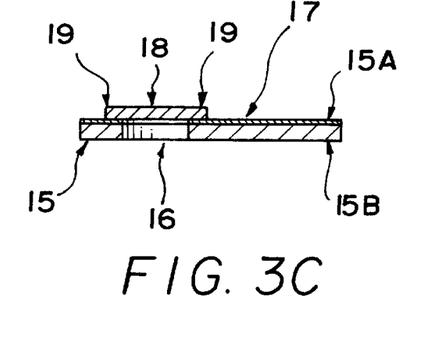
FIG. 3C is an inverted side view of the fabrication of a unit comprising a particularly preferred blood separation (first hydrophilic) layer attached to a hydrophobic material mounted on a solid surface.
Figure 3D:
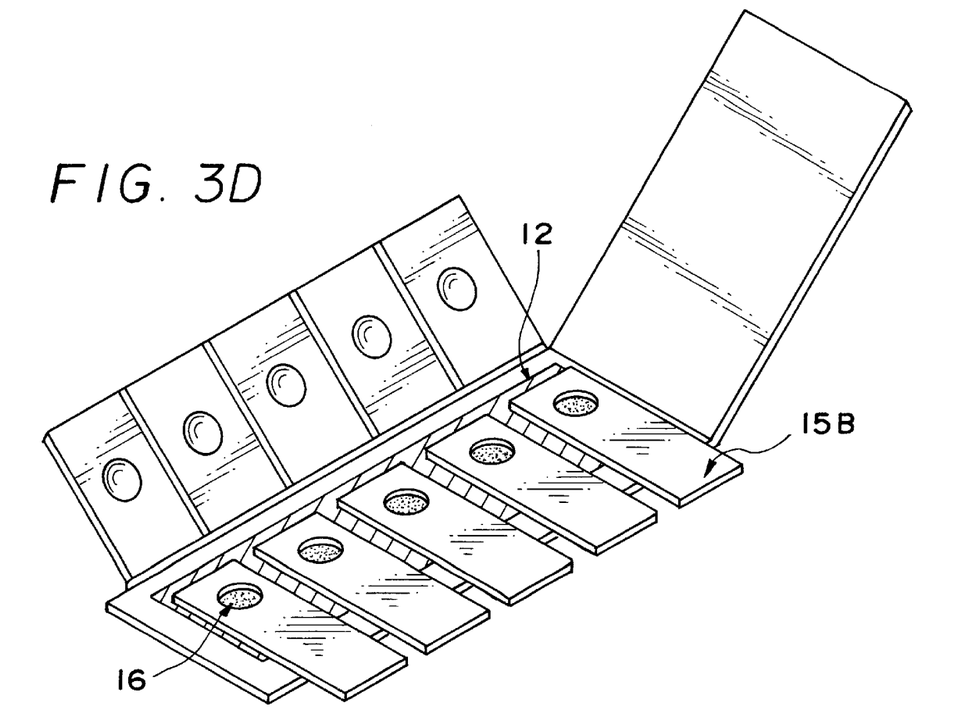
FIG. 3D illustrates the preferred fully assembled device as it appears before application of any whole blood sample.
Figure 3E:
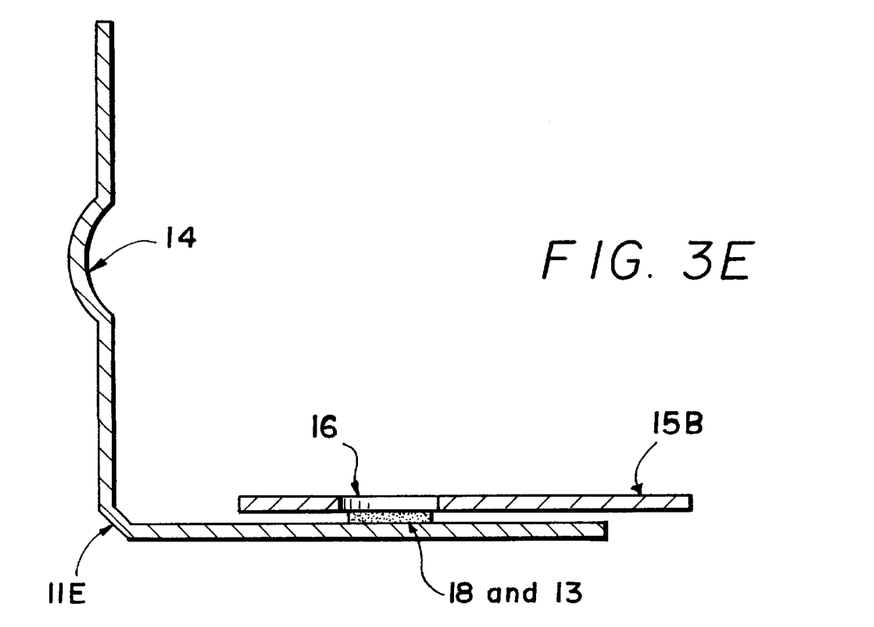
FIG. 3E is a side view of an uncovered receiving station.
Figure 3F:
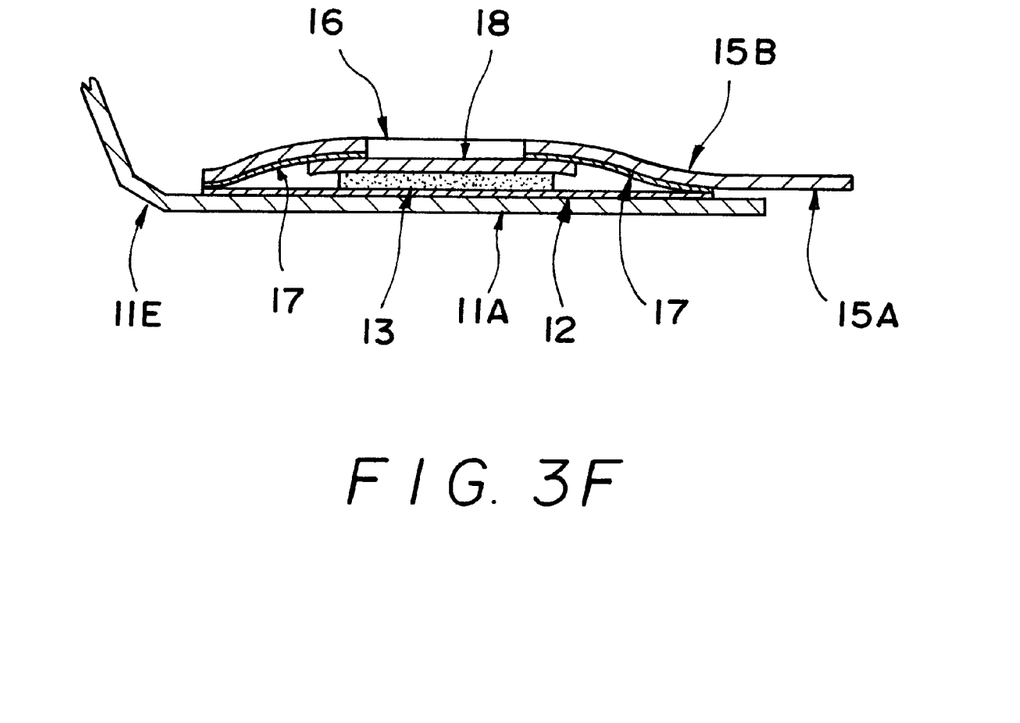
FIG. 3F shows an exaggerated detail of a single blood receiving station, in side view, prior to application of a blood sample
Figure 3G:
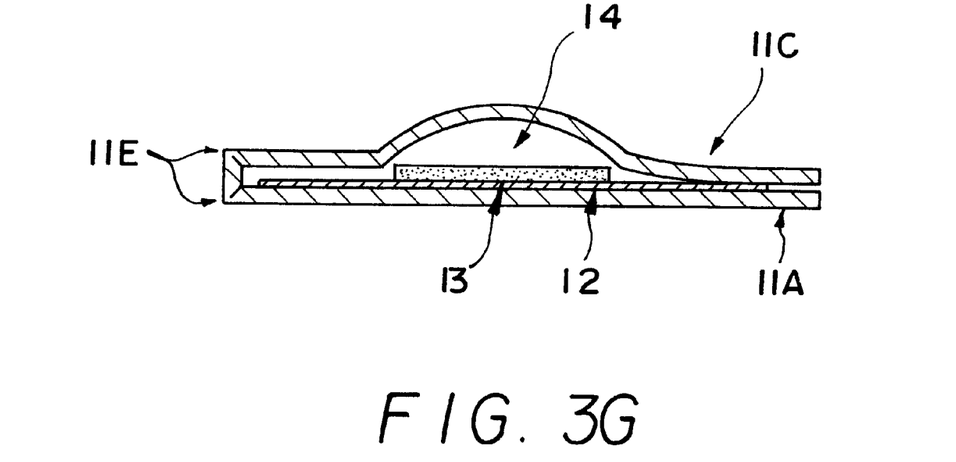
FIG. 3G shows a side view of the same blood receiving station again in exaggerated detail, after stripping away of the two upper layers from the plasma retention pad and lowering of the cover over the station.

Referring to FIGS. 3A to 3G, to further illustrate details of a device of this invention having five receiving stations, 24 point chipboard is cut to form all items bearing the "11" numeral in FIG. 3A. These include a device base section 11A, a "matchbook"-like flap labelled 11B and 5 individual sample covers in a device top portion divided into 5 segments each labelled 11C.

The segmented top 11C is double folded at edge 11E in such a way that each of the five segments may be individually folded over bottom portion 11A to cover one of the exposed plasma retention pads upon completion of the blood sample delivery and separation and the plasma isolation process at that station. In each segment a dome 14 of a diameter larger than the corresponding plasma sample retention pad (second hydrophilic layer) 11A has been embossed.

In assembling the device the bottom ("second") hydrophobic layer comprising wide, double sided hydrophobic adhesive plastic tape 12 from Minnesota Mining and Mfg. Co. is applied along the length of 11A, spaced apart from fold line 11E and parallel to it. Filter paper, Ahlstrom 601 is punched into appropriately sized discs to form the lower ("second") hydrophilic layer (i.e., the plasma retention layer) of each sample receiving station. The discs 1B are each located at even intervals along the hydrophobic tape 12, such that their centers and those of the domes 14 will align when the 11C sections are folded over to cover the isolated plasma samples.

Cytosep 1660 from Ahlstrom, Inc. of Mt. Holly Springs, Pa. is impregnated by coating with a mixture of 50 mg. of phytohemagglutinin P (obtained from Phaesolus vulgaris and supplied by Difco) and 450 mg. of Hexadimethrine bromide (obtained from Aldrich Chemical Co.) per square foot of the Cytosep. After coating, the Cytosep, which comprises the upper (first) hydrophilic layer that acts to separate red blood cells from plasma or serum, is dried and punched into discs 18 of slightly larger diameter than discs 13. These discs 18 are centered over discs 13 in the following manner: 24 point chipboard is coated on one side (labelled 15A in FIGS. 3A to 3G) with a polyethylene layer 17 and cut into five suitably sized strips. A hole of slightly smaller diameter than discs 18 is punched into each of the strips 15 at locations which are centered so that they would fall beneath each of the domes 14 if the device were closed. Each agglutinant coated Cytosep disc 18 is heated around its edge 19 while being pressed against polyethylene layer 17 to seal it to one of the coated chipboard sections 15 at a position that is centered over hole 16. Each chipboard section 15 is then positioned so that hole 16 and Cytosep disc 18 are centered over one of the filter paper discs 13 with the Cytosep surface in abutting contact with the filter paper, while the polyethylene coated side 15A of each chipboard section 15 is pressed against adhesive tape 12 to anchor it in place. Thus the "sandwich" of blood separation layer 18 in contact with plasma isolation/retention layer 13 surrounded by upper and lower hydrophobic layers 17 and 12 is fabricated at each sample receiving station. For shipping and/or storage, the protective covers 11C are folded over the respective stations and the flap 11B is folded over the closed covers.

To use the device, one folds flap 11B and a protective cover 11C containing a domed cover 14 back and applies a drop of blood to hole 16. After a minimum of 2 minutes and a maximum of ten minutes, the portion of section 15 that overhangs base 11A is grasped and peeled off, thereby isolating plasma sample retention pad 13. Protective cover 11C containing domed cover 14 is then closed over pad 13. By virtue of double fold 11E and dome 14, sample retention pad 13 is not sealed shut but remains in contact with air so that the plasma on pad 13 dries.

When plasma has been transferred to all of the pads 13 and they have all been isolated as described and covered, the flap 11B is again closed over protective covers 11C and the device is sealed in a foil pouch with desiccant for transport to a laboratory. Upon arrival there, the sample retention pads 13 are removed from adhesive strip 12 and the plasma is extracted into a suitable medium for analysis or assay.

Obviously, there are many possible ways of constructing the device of this invention. The foregoing specific description keyed to illustrative FIGS. 3A to 3G is not meant to limit in any way the possible embodiments of the invention that meet the criteria described hereinabove for specific materials, nor is it intended to limit the choice of obvious alternative geometries, support materials, agglutinating or clotting agents, sizes, shapes or the like.

One of the surprising benefits of using the devices of this invention was the realization that plasma or serum dried on a material that meets the criteria disclosed herein for the second (bottom) hydrophilic layer that receives and retains a defined volume of plasma or serum is that the constituents of the plasma thus air dried are highly stable.

The following examples serve to illustrate this stability, other benefits that follow from using this invention, and certain critical limitations of the invention or its use:

EXAMPLE 1

The surprising stability of blood plasma constituents air dried on filter paper is illustrated in this example.

In this experiment, a sample of EDTA-anticoagulant-treated blood was used to compare the stability of some constituents of blood plasma. One portion of this blood was centrifuged at 1,500×g for 10 minutes and the clear plasma was separated from the red cells. Replicate 6.00-$\mu$L. aliquots of this plasma were pipetted onto filter paper discs (13 as described above by reference to FIGS. 3A to 3G), mounted on a hydrophobic tape attached to a cardboard support, and the plasma was allowed to air dry. These discs were sealed into a foil pouch with a silica desiccant pack and left to incubate. At the same time, aliquots of the same whole blood and of the isolated plasma were sealed into microfuge tubes and also left to incubate at room temperature. A portion of the clear plasma as freshly separated was assayed on the day of its separation by centrifugation for its content of lactic acid, glucose and lactate dehydrogenase. After 7 days storage at room temperature, the whole blood was centrifuged to obtain plasma, and this plasma, the air dried plasma, and the stored liquid plasma samples were assayed for the same constituents. The results are shown in Table 1. The whole blood sample was difficult to analyze for lactate and glucose due to the coloration of the sample by hemoglobin.

When the experiment is repeated, but the incubation is performed at 50° C., the results are obtained as shown in Table 2. Clearly, air drying of plasma on a suitable hydrophilic support is the best mode of preserving its constituents.

TABLE 1

Recovery of plasma constituents after 7 days at room temperature

| Medium | Lactate (mM) | % | Glucose (mM) | % | LDH $\mu$/L | % |
|---|---|---|---|---|---|---|
| Day 0, Plasma | 0.81 | 100 | 4.1 | 100 | 102 | 100 |
| Day 7, Plasma | 0.86 | 106 | 4.0 | 98 | 80 | 78 |
| Day 7, Blood Plasma | 3.8 | 469 | 1.3 | 32 | 256 | 251 |

TABLE 1-continued

Recovery of plasma constituents after 7 days at room temperature

| Medium | Lactate (mM) | % | Glucose (mM) | % | LDH μ/L | % |
|---|---|---|---|---|---|---|
| Day 7, Dried Plasma | 0.78 | 96 | 4.0 | 98 | 107 | 105 |

TABLE 2

Recovery of plasma constituents after 7 days at 50° C.

| Medium | Lactate (mM) | % | Glucose (mM) | % | LDH μ/L | % |
|---|---|---|---|---|---|---|
| Day 0, Plasma | 0.81 | 100 | 4.1 | 100 | 102 | 100 |
| Day 7, Plasma | 0.74 | 91 | 3.5 | 85 | <15 | Not Detected |
| Day 7, Blood Plasma | 4.9 | 605 | <0.1 | Not Detected | <15 | Not Detected |
| Day 7, Dried Plasma | 0.83 | 102 | 3.9 | 95 | 97 | 95 |

EXAMPLE 2

A set of 20 replicated plasma samples, prepared as described in relation to FIGS. 3A–3G, were obtained from 30 μL. drops of citrate-anticoagulated blood. Simultaneously, an aliquot of the whole blood was centrifuged to prepare plasma, and this plasma was immediately analyzed for its content of L-lactate. From this analysis, a standard curve was prepared in a known manner, relating content of L-lactate to plasma volume. After air drying the plasma retention discs of this invention, the discs were eluted with a buffer containing 50 mM MOPS of pH 7.4, 0.1% Bovine Serum Albumin (BSA), and 0.1% Triton X-100. The eluate was assayed for lactate and the average volume of plasma contained on the discs was calculated from a comparison of the lactate response results to those of the plasma-volume standard curve.

The experiment was repeated with EDTA-anticoagulant-treated blood spiked with 1 mM 4-aminoantipyrine as reporter molecule. These results are all shown in Table 3.

TABLE 3

Volume of Plasma Recovered from the instant invention (n = 20)

| Volume Determination by: | Mean Volume (μL) | Standard Deviation (μL) | Coefficient of Variation (CV) |
|---|---|---|---|
| Lactate | 5.68 | 0.31 | 5.4 |
| 4-Amino-antipyrine | 5.83 | 0.21 | 3.6 |

EXAMPLE 3

Experiment 2 was repeated with ten replicated plasma samples each, but the following changes in the devices were made.
  A. Instead of covering the support base 11A of FIGS. 3A to 3G with double sided plastic tape 12, such tape was used only directly under the plasma absorption disc 13 thus exposing the paper covered surface of 11A adjacent to the disc 13. A section 15 with attached disc 18 was spot glued to the support 11A at points above and below hole 16, and about 1 cm. away from the hole.
  B. Instead of using double sided plastic tape 12 of FIGS. 3A to 3G, disc 13 was attached to support 11A with Elmer's glue gel, a water soluble glue that leaves a hydrophilic surface when dried, or with Borden's neoprene-based contact cement, an adhesive that also leaves a hydrophilic surface. A section 15 with attached disc 18 was spot glued to 11A as in A part hereof, above.
  C. Instead of heat sealing treated Cytosep 8 to a polyethylene coating on support surface 5A, the circumference of the Cytosep was glued to the uncoated paper surface of 5A using Duco cement.
  D. Cytosep disc 8 was only sealed to surface 5A at 4 spots, so that its circumference was not completely sealed to polyethylene coating 7, and hence gaps were present.

When devices constructed as in A, B or C were tested for the reproducibility of the plasma volume captured, the coefficients of variation of the captured volume varied from 7 to 11%, and this was considered unacceptable for a quantitative analysis. Devices constructed according to section D above were badly contaminated with red blood cells from leakage of blood around the edge of disc 8. These devices failed to perform the required red cell-plasma separation.

These results illustrate the benefit of surrounding the plasma capture disc-red cell separation matrix with a hydrophobic surface, to foster the reproducibility of plasma uptake into the plasma capture medium. It also illustrates the critical requirement to completely seal the blood cell separation medium to its support tab, so that red blood cells must pass into the separation medium and not pass around it.

EXAMPLE 4

Devices constructed as in Example 2 are developed with whole blood, except for three variations:
  A. devices were supplied with blood drops varying from 17 to 70 μL in volume;
  B. The time that blood was in contact with the device before isolation of the plasma sample was varied from 1.5 to 5 minutes;
  C. Prior to applying the blood to the device, the hematocrit of the blood was adjusted to varying levels between 35 and 57%.

TABLE 4

Changes in Average Percent Recovery and CV of the nominal (5.7 μL) plasma sample volume in response to changes in:

| A. Blood Volume (μL) | Percent Recovery | Coefficient of Variation |
|---|---|---|
| 17 | 87 | 6.7 |
| 20 | 92 | 5.3 |
| 25 | 100 | 4.7 |
| 30 | 100 | 3.0 |
| 70 | 102 | 5.9 |

| B. Time on Device (min) | Percent Recovery | Coefficient of Variation |
|---|---|---|
| 1.0 | 92 | 4.2 |
| 1.5 | 92 | 3.6 |
| 2.0 | 100 | 4.3 |
| 3.0 | 100 | 3.3 |
| 5.0 | 104 | 3.9 |

TABLE 4-continued

| C. Hematocrit | Percent Recovery | Coefficient of Variation |
|---|---|---|
| 57 | 87 | 11 |
| 53 | 96 | 4.6 |
| 48 | 102 | 3.5 |
| 41 | 100 | 2.9 |
| 36 | 108 | 4.8 |

A. Whole blood sample volume,
B. Duration of blood incubation on the device before isolation of plasma; and
C. Hematocrit of the blood.
The average volume of plasma captured in tests A and B was essentially constant as shown in Table 4. In test C, the plasma volume captured was constant up to a hematocrit level of 53 but the captured volume was reduced significantly when blood of hemacrit 57 was used.

This example illustrates that the devices will operate reliably in the hands of untrained users, without a need for precisely measuring the whole blood sample volume, or precisely timing the period between blood sample application to the device and the isolation of the plasma retention disc from the blood separation disc. In the latter instance, other work has shown intervals of from two to ten minutes between blood sample application and plasma retention disc isolation give satisfactory results within the limits of experimental error. Intervals of two to five minutes are, however, preferred.

The example also shows the device will work satisfactorily with blood samples of hematocrit from 35 to 53. The blood of at least 99% of the human population has a hematocrit less than 57, according to C. Lentner, Ed., *Geigy Scientific Tables*, Vol. 3, p. 207 (CIBA-GEIGY: Basle).

EXAMPLE 5

To devices prepared as in Example 2 whole blood spiked with 1 mM lithium chloride and 1 mM sodium salicylate is applied. Plasma samples prepared by immediate centrifugation of this blood are compared to plasma isolated in the devices of the invention, allowed to dry and stored for 7 days in sealed, desiccated foil pouches. The following plasma components are recovered essentially quantitatively from the device plasma samples: Lactate dehydrogenase, lactic acid, glucose, cholesterol, anti-hepatitis B antibodies, insulin, lithium, salicylate and TSH.

It is anticipated that the following possible plasma components of plasma isolated and air dried in devices of this invention will similarly be essentially quantitatively recoverable: Alanine aminotransferase, Creatine kinase, Glutamate oxalacetate transaminase. Alkaline phosphatase, Plasma renin, Glucose-6-phosphate uridyl transferase, Plasma ACTH, Luteinizing hormone, Calcitonin, Cortisol, Catecholamines, Androstenedione, Atrial natiuretic factor, Glucagon, Progesterone, Testosterone, Estrogen and its metabolites, Estriol, Triglycerides, Ammonia, Vitamin C, Zinc, Antinuclear antibodies, Anti-DNA antibodies, Extractable nuclear antigen antibodies, Antimitochondrial antibodies, Anti-smooth muscle antibodies, Antithyroid antibodies, Thyroid-stimulating immunoglobulins, Cardiolipin antibodies, Rheumatoid factor, Acetylcholine receptor antibodies, Rubella antibodies, Anti-HIV antibodies, Anti-CMV antibodies, Hepatitis B surface antigen, EBV antibodies, RSV antibodies, Herpes simplex antibodies, Antifungal antibodies, Anticandida antibodies, Bacterial meningitis antigen, Lyme disease antibodies, Syphilis antibodies, CEA, AFP, hCG, ACTH, Prostatic acid phosphatase, Prostate specific antigen, Tissue polypeptide antigen, Tenagen (Tennessee Antigen), Pregnancy-specific glycoprotein, Serotonin, Amikacin, Caffeine, Carbamazepine, Chloramphenicol, Desipramine, Digoxin, Diisopyramide, Ethosuccinimide, Gentamicin, Imipramine, Lidocaine, Methotrexate, Phenobarbital, Phenytoin, Primidone, Procainamide, NAPA, Quinidine, Theophylline, Tobramycin, Valproic acid, Pseudo-cholinesterase, Mercury, Arsenic, Antimony, Selenium, and Bismuth.

It is emphasized that many variations in the devices of this invention, which will be readily apparent to those skilled in the art, can be made without departing from the scope of the invention. It is accordingly intended that the scope of this invention be limited only by the appended claims.

What is claimed is:

1. A process for separating plasma or serum from mammalian whole blood which comprises the steps of:
   (a) applying a sample of said blood through a hydrophobically faced sample receiving hole positioned in a first, upper layer of hydrophobic material to a first layer of fibrous hydrophilic material which has been impregnated with a blood agglutinating or clotting agent so that it acts to retain red blood cells but not plasma or serum, which layer is sealed at its upper edges to said first layer of hydrophobic material; and
   (b) allowing the liquid portion of said sample to flow downwardly through said first layer of fibrous hydrophilic material into a second layer comprised of a different fibrous hydrophilic material which second layer is sealed at its lower edges to a second layer of hydrophobic material whereby said second layer comprised of a different fibrous hydrophilic material acts to retain the plasma or serum.

2. The process of claim 1 in which the sample size is one drop.

3. The process of claim 1 in which the first hydrophobic layer and the first hydrophilic layer are stripped away from the second hydrophilic layer after a period of about ten minutes.

4. The process of claim 3 in which the period is about five minutes.

5. The process of claim 3 wherein the serum or plasma contained in the second hydrophilic layer is allowed to dry in said layer and set aside, or sent elsewhere, to be immunoassayed for at least one component suspected or known to be present.

6. The process of claim 5 wherein the second hydrophilic layer is stripped from the second hydrophobic layer and the dried serum or plasma contained in the second hydrophilic layer is extracted into a suitable liquid medium prior to assay.

7. The process of claim 6 wherein, after stripping away the second hydrophobic layer, the second hydrophilic layer is placed in contact with the reaction pathway of an immunoassay device and wetted with a buffer or other suitable liquid to extract the plasma or serum contained in said second hydrophilic layer and cause it to migrate along the said reaction pathway.

8. A process in which multiple blood samples, each consisting of a single drop of blood, are taken from a human subject at defined time intervals and each sample is subjected to the process of claim 3, using in each instance a separate assembly of said first hydrophobic layer, said first hydrophilic layer impregnated with blood agglutinating or clotting agent, said second hydrophilic layer and said second hydrophobic layer, whereby the second hydrophilic layer of each separate assembly captures a defined volume of serum or plasma, the serum or plasma contained in each of the second hydrophilic layer components of the separate assemblies is allowed to dry and the separate second hydrophilic layer and the associated second hydrophobic layer components of each assembly are conveyed to a laboratory wherein:

(a) the second hydrophobic layer of each assembly is stripped from the associated second hydrophilic layer and discarded, (b) the second hydrophilic layer is treated with liquid to extract the plasma or serum therefrom and the plasma or serum is assayed for the presence of at least one known or suspected component.

* * * * *